United States Patent
Kauppinen et al.

(10) Patent No.: US 11,679,273 B2
(45) Date of Patent: Jun. 20, 2023

(54) METHOD AND APPARATUS TO DELIVER THERAPEUTIC RADIATION TO A PATIENT USING FIELD GEOGRAPHY-BASED DOSE OPTIMIZATION

(71) Applicant: Siemens Healthineers International AG, Steinhausen (CH)

(72) Inventors: Juha Kauppinen, Espoo (FI); Anthony Magliari, Newark, IL (US); Martin Sabel, Hagendorn (CH); Amir Talakoub, Austin, TX (US)

(73) Assignee: Siemens Healthineers International AG, Steinhausen (CH)

( * ) Notice: Subject to any disclaimer, the term of this patent is extended or adjusted under 35 U.S.C. 154(b) by 288 days.

(21) Appl. No.: 17/031,097

(22) Filed: Sep. 24, 2020

(65) Prior Publication Data

US 2022/0088411 A1  Mar. 24, 2022

(51) Int. Cl.
*A61N 5/10* (2006.01)
*G01T 1/02* (2006.01)

(52) U.S. Cl.
CPC ......... *A61N 5/1031* (2013.01); *A61N 5/1045* (2013.01); *A61N 5/1048* (2013.01); *A61N 5/1081* (2013.01); *G01T 1/02* (2013.01)

(58) Field of Classification Search
CPC .............. A61N 5/103–1039; A61N 2005/1041
See application file for complete search history.

(56) References Cited

U.S. PATENT DOCUMENTS

| | | | |
|---|---|---|---|
| 10,092,774 B1* | 10/2018 | Vanderstraten | G16H 10/60 |
| 2003/0138077 A1 | 7/2003 | Lee | |
| 2009/0088625 A1* | 4/2009 | Oosting | A61N 5/1084 |
| | | | 600/425 |
| 2013/0131430 A1* | 5/2013 | Froehlich | A61N 5/1042 |
| | | | 600/1 |
| 2017/0274224 A1 | 9/2017 | Petäjä et al. | |
| 2018/0085596 A1 | 3/2018 | Peltola et al. | |

OTHER PUBLICATIONS

International Search Report and Written Opinion from related International Application No. PCT/EP2021/075530 dated Jan. 18, 2022; 18 pages.

* cited by examiner

*Primary Examiner* — Thaddeus B Cox
(74) *Attorney, Agent, or Firm* — Fitch, Even, Tabin & Flannery LLP

(57) ABSTRACT

These teachings provide for accessing optimization information comprising at least one isocenter that corresponds to a body outline for a particular patient, field geometry information for a particular radiation treatment platform, and dosimetric data. The optimization information can further comprise a model of a body outline for the patient. A control circuit optimizes a radiation treatment plan as a function of the optimization information to provide an optimized radiation treatment plan where radiation dose levels delivered to the particular patient from a particular field depends on the relative volume magnitude of field path intersections to thereby reduce radiation dose delivery to healthy patient tissue in regions having relatively more overlapping fields.

18 Claims, 6 Drawing Sheets

METHOD AND APPARATUS TO DELIVER THERAPEUTIC RADIATION TO A PATIENT USING FIELD GEOGRAPHY-BASED DOSE OPTIMIZATION

TECHNICAL FIELD

These teachings relate generally to treating a patient's planning target volume with radiation pursuant to a radiation treatment plan and more particularly to optimizing a radiation treatment plan.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted material and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Unfortunately, the radiotherapy field setups specified by a given radiation treatment plan can sometimes deliver relatively high radiation dosing to healthy tissue in regions where multiple field paths overlap. This problem can occur in both forward planning techniques and also to some extent in inverse planning techniques.

BRIEF DESCRIPTION OF THE DRAWINGS

The above needs are at least partially met through provision of the method and apparatus to facilitate generating a deliverable therapeutic radiation treatment plan described in the following detailed description, particularly when studied in conjunction with the drawings, wherein.

Figure 1:
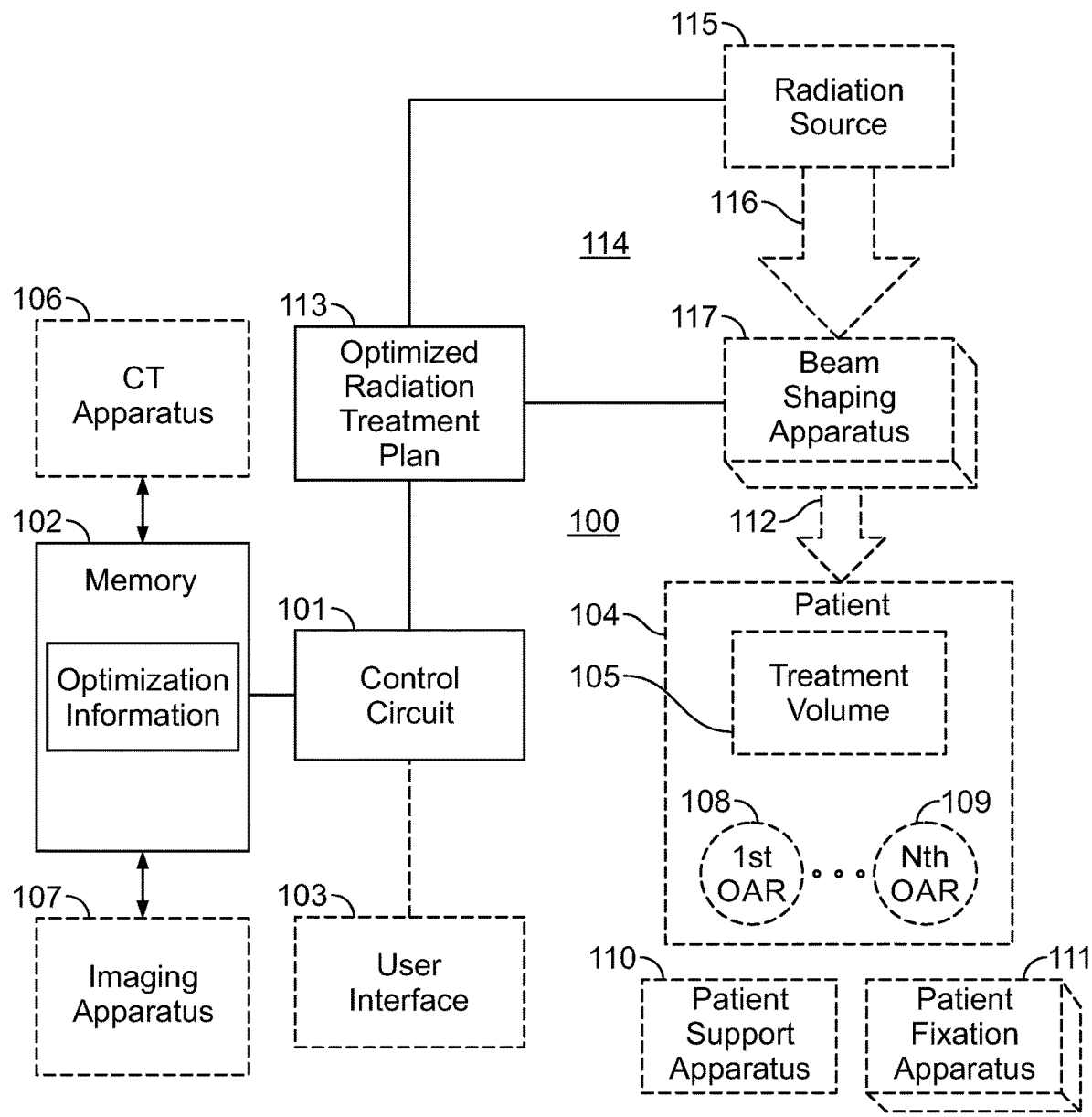
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate radiating a treatment target in a patient during a radiation treatment session with a radiation treatment platform having a moving source of radiation and using an optimized radiation treatment plan. By one approach, these teachings provide for accessing, via a control circuit, optimization information. This optimization information can comprise, for example, at least one isocenter that corresponds to a body outline for a particular patient, field geometry information for a particular radiation treatment platform, and dosimetric data. If desired, the optimization information can further comprise a model of a body outline for the particular patient.

The control circuit can then optimize a radiation treatment plan for that particular patient and using that particular radiation treatment platform as a function, at least in part, of the foregoing optimization information to thereby provide an optimized radiation treatment plan where radiation dose levels delivered to the particular patient from a particular field depends on the relative volume magnitude of field path intersections to thereby reduce radiation dose delivery to healthy patient tissue in regions having relatively more overlapping fields.

By one approach, the foregoing information regarding the at least one isocenter that corresponds to the body outline comprises a plurality of isocenters that all correspond to that body outline.

By one approach, the foregoing field geometry information represents, at least in part, a trajectory of a radiation source during administration of the radiation treatment plan. These teachings are flexible in practice, and will accommodate field geometry information corresponding, for example, to one or more of static-gantry fields, arc fields, fields with stereotactic radiosurgery cones, static-multi-leaf collimator fields, and dynamic-multi-leaf collimator fields.

And by one approach, the aforementioned dosimetric data only includes at least one of depth-dose profile data and depth-penumbra data and no other dosimetric data is so utilized.

If desired, these teachings will also accommodate configuring the control circuit to determine relative radiation dose levels as a function of the relative magnitudes of intersection volumes of field paths within healthy tissue. Additionally, and also if desired, the control circuit can be configured to determine the aforementioned intersection volumes as a function, at least in part, of geometrical solutions for common volumes of intersecting cylinders.

These teachings will then accommodate operating the aforementioned particular radiation treatment platform as a function of the optimized radiation treatment plan to administer therapeutic radiation to the particular patient.

So configured, the overdosing of healthy tissues can be at least reduced in regions where field paths overlap.

These and other benefits may become clearer upon making a thorough review and study of the following detailed description. Referring now to the drawings, and in particular to FIG. 1, an illustrative apparatus 100 that is compatible with many of these teachings will be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization information such as isocenter location(s), field geometry information, dosimetric data, and so forth, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms/apparatuses. In a typical application setting the radiation treatment platform 114 will include a radiation source 115 that can be selectively moved via a gantry along an arcuate pathway. The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

The radiation source 115 can comprise, for example, a radio-frequency (RF) linear particle accelerator-based (linac-based) x-ray source, such as the Varian TrueBeam or Halcyon linear accelerator. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. In a typical application setting, it is presumed herein that the patient support apparatus 110 is selectively controllable to move in any direction (i.e., any X, Y, or Z direction) during a radiation treatment session by the control circuit 101. As the foregoing elements and systems are well understood in the art, further elaboration in these regards is not provided here except where otherwise relevant to the description.

Figure 2:
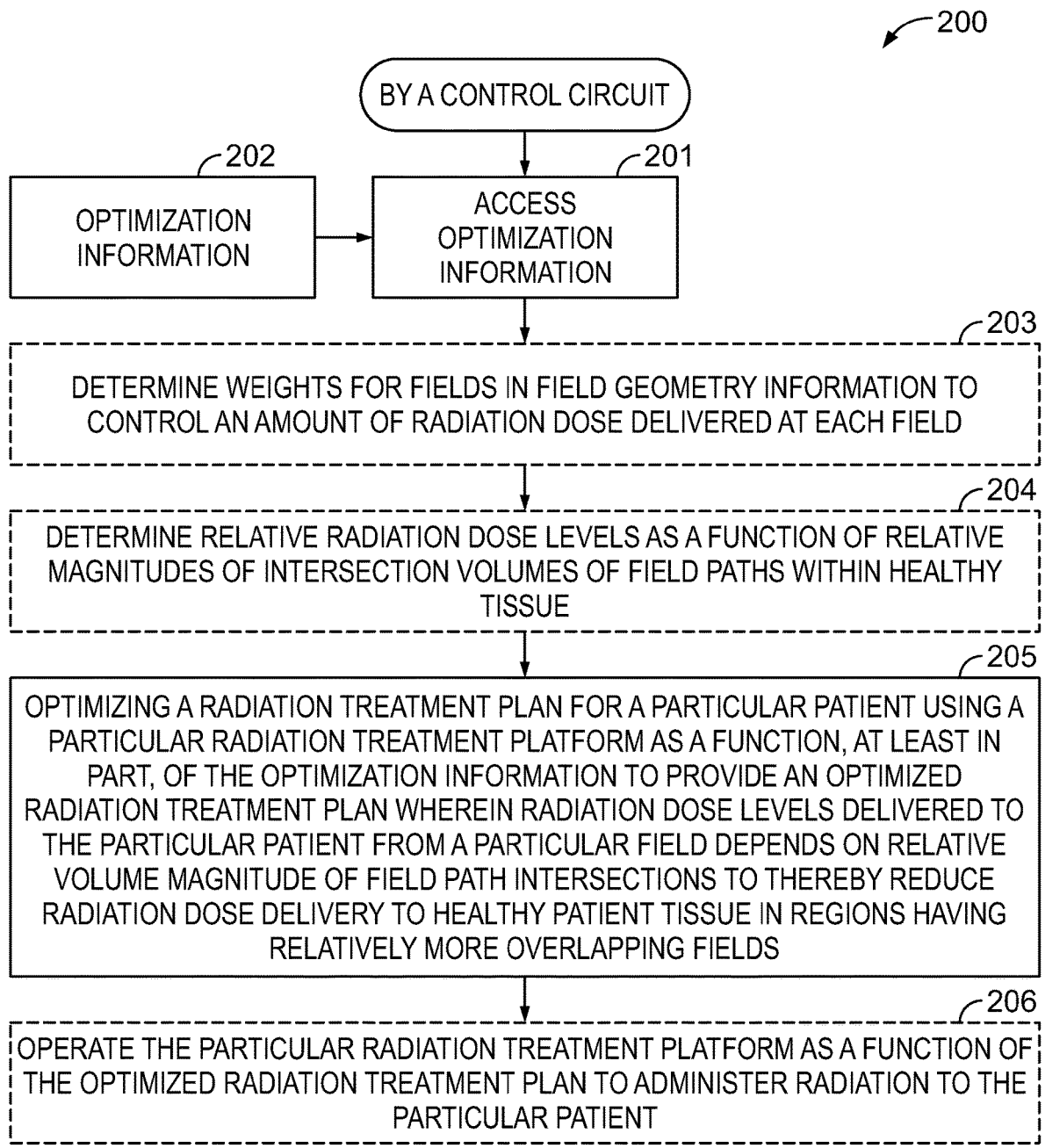
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate radiating a treatment target (105) in a patient (104) during a radiation treatment session with a radiation treatment platform (114) having a moving source of radiation (115) using an optimized radiation treatment plan (113).

At block 201, this process 200 can access optimization information 202. By one approach, this optimization information 202 comprises information regarding a relative location of at least one isocenter that corresponds to a body outline for a particular patient 104, field geometry information for a particular radiation treatment platform 114, and dosimetric data. In many application settings the optimization information 202 may also include a model of a body outline for the particular patient 104.

Those skilled in the art of radiotherapy know that an isocenter is the point in space through which the center of a beam of radiation passes, especially when the beam of radiation moves with respect to the patient. In many cases, the isocenter is the point in space relative to a radiation treatment platform about which a source of radiation rotates via a gantry. In a typical application setting the isocenter will be located within the treatment volume 105 (for example, more or less at the center of the volume 105). It should be noted that this process 200 will accommodate a plurality of isocenters that correspond to the patient's body outline in an appropriate application setting.

The aforementioned field geometry information can vary with the needs and/or opportunities presented by the physical characteristics of a given radiation treatment platform 114. In many cases and generally speaking, the field geometry information represents, at least in part, a trajectory of the radiation source 115 during administration of the radiation treatment plan 113. More specifically, the field geometry information can correspond to at least one, many, or all of static-gantry fields, arc fields, fields with stereotactic radiosurgery cones, static-multi-leaf collimator fields, and dynamic-multi-leaf collimator fields. (As used herein, the expression "field" will be understood to include both "fields" and "subfields," where either or both may be available depending upon the treatment platform and/or the treatment modality itself.)

The aforementioned dosimetric data can vary as well with the needs and/or opportunities that characterize a given application setting. By one approach, the dosimetric data can be limited in scope and include only one or both of depth-dose profile data and depth-penumbra data. In such a case, the optimization information 202 includes no other dosimetric data to be utilized by the control circuit 101/process 200.

At optional block 203, if desired, the control circuit 101 can determine weights for the fields in the field geometry information to thereby facilitate control of an amount of radiation dose to be delivered at each field and to use some or all of those weights when optimizing the radiation treatment.

And at optional block 204, if desired, the control circuit 101 can determine relative radiation dose levels as a function of relative magnitudes of intersection volumes of field paths within healthy tissue (such as the aforementioned organs at risk 108, 109). By one approach, the control circuit 101 can determine such intersection volumes as a function, at least in part, of geometrical solutions for common volumes of intersecting cylinders.

In any event, at block 205 the control circuit 101 optimizes a radiation treatment plan for the particular patient 104 using the particular radiation treatment platform 114 as a function, at least in part, of the optimization information 202 to provide an optimized radiation treatment plan 113 wherein radiation dose levels delivered to the particular patient 104 from a particular field depends on relative volume magnitudes of field path intersections to thereby reduce radiation dose delivery to healthy patient tissue in regions having relatively more overlapping fields.

This process 200 can include, as illustrated at optional block 206, then operating the particular radiation treatment platform 114 as a function of the optimized radiation treatment plan 113 to administer radiation to the particular patient 104.

Figure 3:
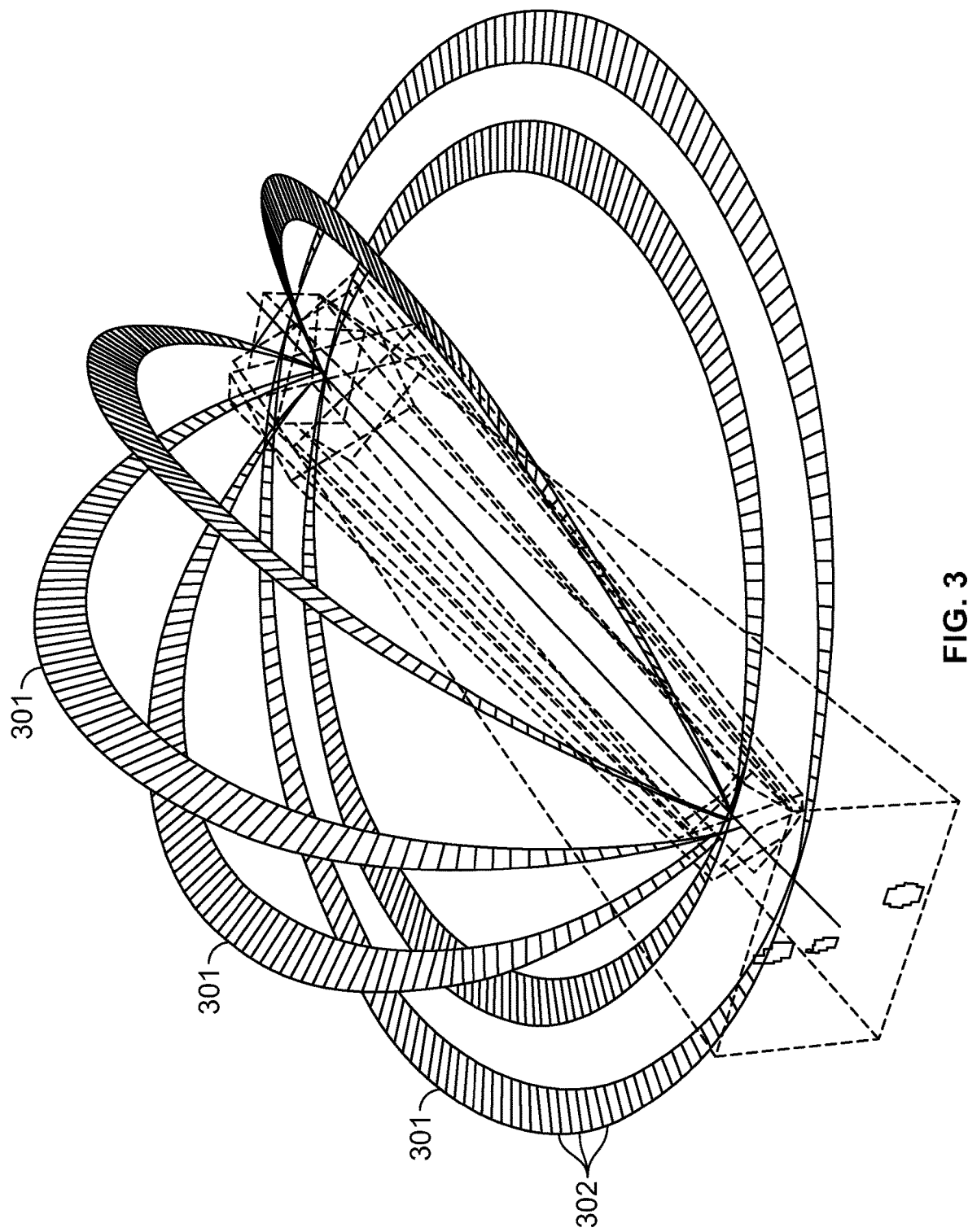
FIG. 3 comprises a schematic view as configured in accordance with various embodiments of these teachings.

As a result, these teachings permit providing different doses of radiation in different fields to help minimize exposing organs at risk to undue dosing that might otherwise occur as a result of overlapping fields. FIG. 3 provides a simple illustrative example in these regards, where each of a plurality of arcs (where some of the arcs are denoted by reference numeral 301) is shown to be comprised of a plurality of fields (where some of the fields are denoted by reference numeral 302). In this illustrative example, the length of each field 302 represents a dosing level to thereby illustrate that each arc 301 is comprised of fields having selectively varied levels of dosing. In this example these levels are adjusted, at least in part, as a function of overlap between fields. Generally speaking, the fields evidencing higher levels of dosing are fields that are not overlapping as much with other fields while fields evidencing lower levels of dosing are fields that do overlap to varying extents with other fields.

Some illustrative examples will now be provided. It should be understood that these examples are intended to serve an illustrative purpose and that the details of these examples are not intended to suggest any particular limitations with respect to these teachings.

Figure 4:
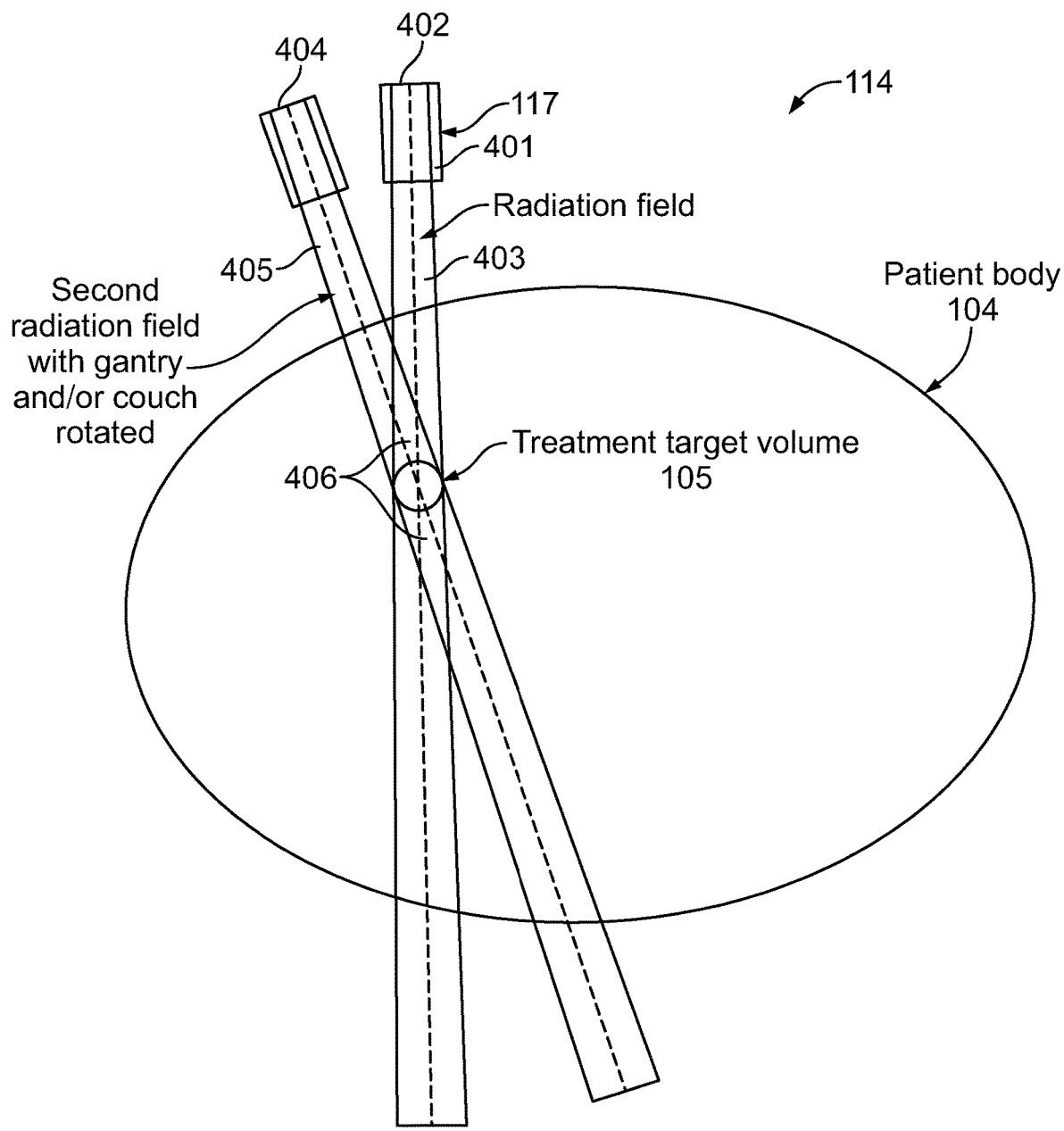
FIG. 4 comprises a schematic view as configured in accordance with various embodiments of these teachings.

Referring to FIG. 4, in this example the radiation treatment platform 114 includes a collimator 401 that comprises a part of the beam shaping apparatuses 117. This collimator 117 may comprise, for example, a stereotactic radiosurgery cone, a static multi-leaf collimator, a dynamic multi-leaf collimator, or otherwise as desired. In a first position denoted by reference numeral 402, the apparatus yields a first radiation field 403. This first radiation field 403 includes the treatment volume 105 within its ambit. After moving counterclockwise to the position denoted by reference numeral 404, the apparatus now yields a second radiation field 405. This second radiation field 405 also includes the treatment volume 105 within its ambit.

Reference numeral 406 denotes volumes within the patient 104 where these two radiation fields 403 and 405 overlap. These teachings serve to decrease the delivered dose of a given subfield in such volumes to thereby minimize the irradiation of untargeted tissue (including, of course, organs at risk).

Figure 5:
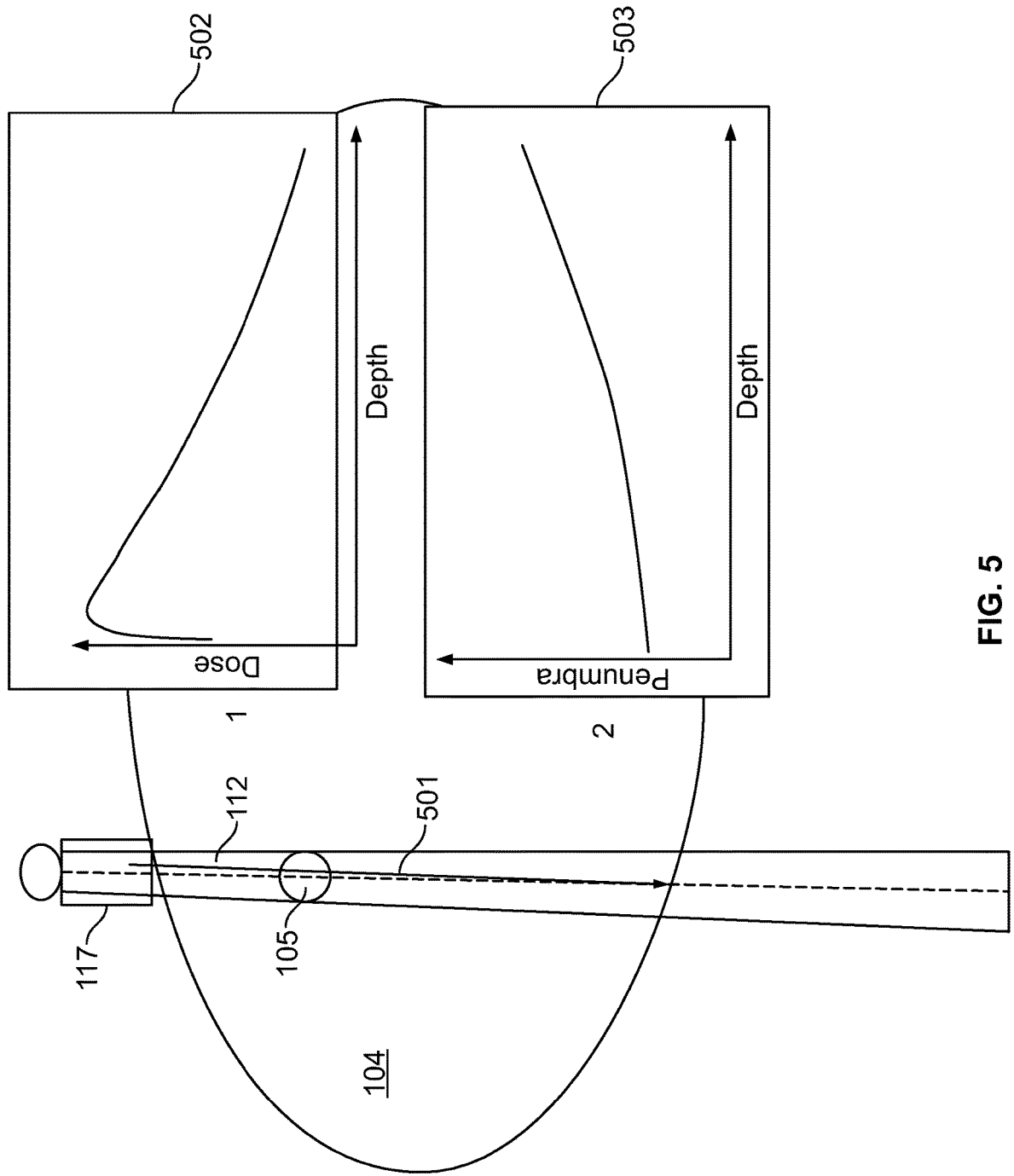
FIG. 5 comprises a schematic view as configured in accordance with various embodiments of these teachings.

By one approach, in lieu of the foregoing or in combination therewith and referring now to FIG. 5, these teachings also support utilizing a depth-dependent dose. In particular, and as represented in graph 502, the dose in this particular subfield is a function of depth such that the dose decreases with increasing depth. (This reference to "depth" refers to the distance the subfield traverses through the patient's body 104.) So configured, this approach helps to avoid undue irradiation of healthy tissue.

By another approach, and again in lieu of the foregoing or in combination therewith, these teachings will support having the delivered dose decrease as the penumbra width at the target depth increases. (Graph 503 depicts a chart where the penumbra width increases with depth.) This approach reduces non-distinct, blurry dose shaping that is associated with a wide penumbra.

With the foregoing in mind, these teachings will support making the following calculations for each field angle in each field.

First, the control circuit 101 can determine a relative intersection volume I that is shared with at least one other field. (In fact, in a typical application setting, such an intersection volume I may be shared, at least in part, with a plurality of other fields.) By one approach this comprises determining an exact volume using, for example, a segment model. By another approach this can comprise making an approximate determination by employing a simplified geometrical solution for the common volume of intersecting cylinders (this approach at least being suitable for single-isocenter setups with circular cones). The target volume is then subtracted from volume I.

The control circuit 101 then determines the depth d of the target volume 105. (In some application settings it may be acceptable to simply determine the depth to the isocenter.)

Using depth-dose profile data (such as graph 502 described above), the control circuit 101 can look up a relative dose level $D_{depth}$ at depth d. And using penumbra data (such as graph 503 described above), the control circuit 101 can look up the relative penumbra width $P_{depth}$ at depth d. The control circuit 101 can then calculate the dose to deliver in this subfield in any of a variety of ways. One useful example is as follows:

Relative dose to deliver=$1-I \times (1-D_{depth})-P_{depth}$.

If desired, these teachings will accommodate applying experimental weights to either or both $D_{depth}$ and $P_{depth}$. Such experimental weights can be determined computationally, for example, by iterating each weight and various target volume locations inside the patient 104 while observing the steepness of the dose fall-off at the boundary of the target volume 105. The steepness can be observed, for example, by generating a dose-volume histogram for the target volume 105 using the complete spatial dose distribution data. The weights resulting in a steepest dose fall-off for a representative set of target volume locations can be used as constant weights in the determination of the foregoing relative dose to deliver.

Figure 6:
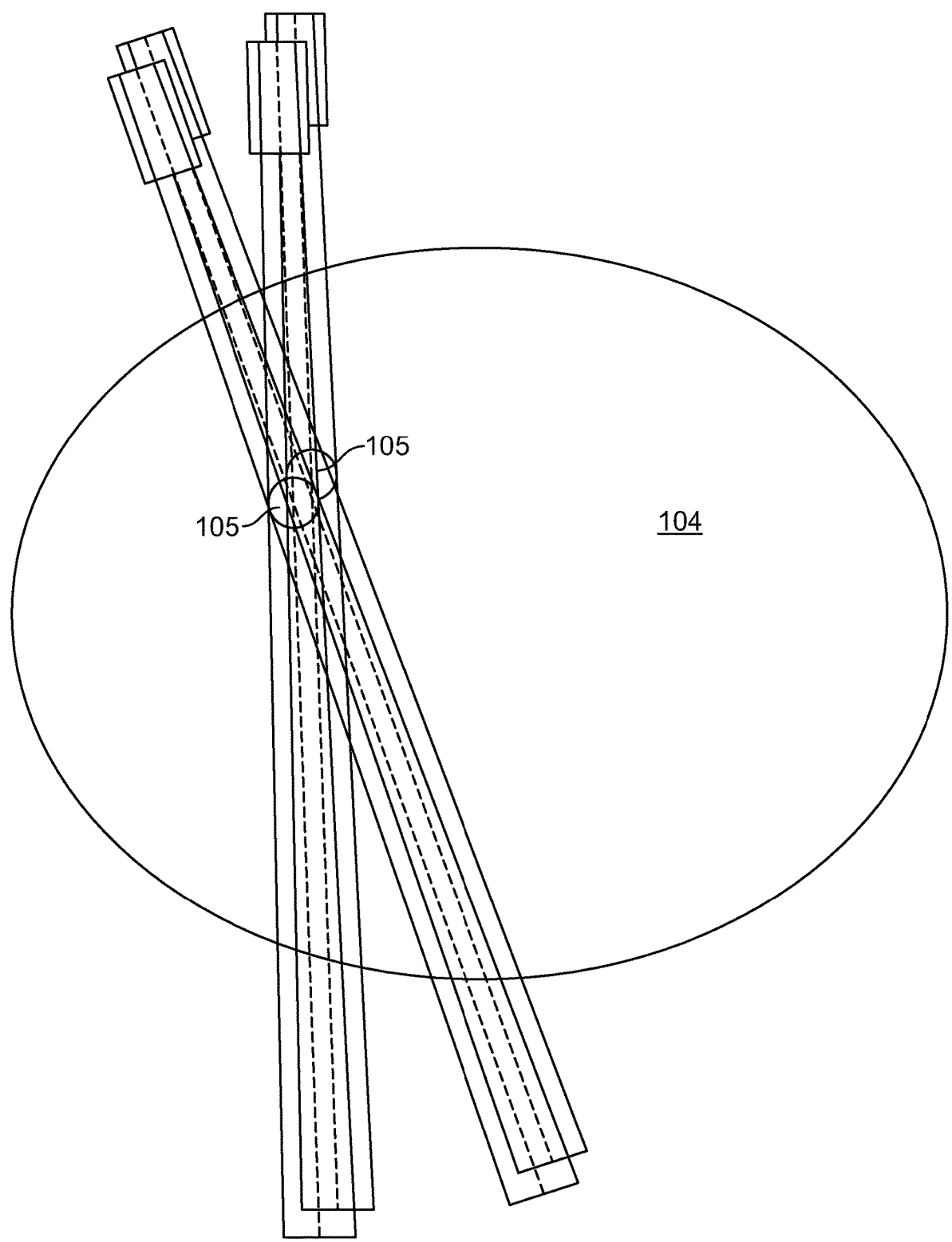
FIG. 6 comprises a schematic view as configured in accordance with various embodiments of these teachings.

FIG. 6 offers an illustrative example where these teachings can be applied in an application setting that makes use of multiple isocenters. In particular, these teachings can provide for enabling dose rate modulation for arc field setups based on multiple isocenters. Multiple isocenters can be used to treat multiple lesions or to cover a single lesion having a large and/or complex shape. Again, these teachings can provide for determining intersection volume sizes by sampling a volume segment model of the field paths.

As one specific illustrative example, these teachings can be employed to facilitate treatment planning and administration using a fanned SRS set up. In particular, the user or apparatus creates an arc or trajectory field set up in a treatment planning phase. For the sake of this example it is presumed that the fields in the field set up overlap significantly within healthy untargeted tissue. The user or apparatus then defines collimation for the fields using SRS cones or static or dynamic multi-leaf collimators. The latter can comprise, for example, choosing an SRS cone size, fitting a multi-leaf collimator to the structure, fit and shield techniques, VMAT optimization, and so forth.

The user or apparatus then applies the foregoing dynamic dose rate teachings. Although these teachings will accommodate manual activities in these regards, these teachings will also accommodate having, for example, a VMAT optimizer integrating the dynamic dose rate techniques in the VMAT fields being optimized. So configured, the apparatus can populate the meterset weights in the control points of the treatment fields that contain the dynamic dose rate data. The apparatus can then calculate the dose distribution for the treatment plan and a user can evaluate the dose distribution and either approve the treatment plan or make further adjustments as desired.

Those skilled in the art will appreciate that these teachings can be employed with optimized inverse planning (such as volumetric modulated arc therapy (VMAT) or intensity-modulated radiation therapy (IMRT)). For example, by one approach these teachings can be integrated with optimized inverse planning techniques so that the corresponding meterset weights primarily follow the dose delivery constraints defined by this process 200.

Those skilled in the art will recognize that a wide variety of modifications, alterations, and combinations can be made with respect to the above described embodiments without departing from the scope of the invention. Accordingly, such modifications, alterations, and combinations are to be viewed as being within the ambit of the inventive concept.

What is claimed is:

1. A method comprising:
   by a control circuit:
   accessing optimization information comprising:
   at least one isocenter that corresponds to a body outline for a particular patient;
   field geometry information for a particular radiation treatment platform; and
   dosimetric data consisting of only depth-penumbra data and no more than one other dosimetric data;
   optimizing a radiation treatment plan for the particular patient using the particular radiation treatment platform as a function, at least in part, of the optimization information to provide an optimized radiation treatment plan wherein radiation dose levels delivered to the particular patient from a particular field depend on relative volume magnitude of field path intersections to thereby reduce radiation dose delivery to healthy patient tissue in regions having relatively more overlapping fields; and
   operating the particular radiation treatment platform as a function of the optimized radiation treatment plan to administer radiation to the particular patient.

2. The method of claim 1 wherein the dosimetric data only includes:
   depth-dose profile data; and
   the depth-penumbra data.

3. The method of claim 1 wherein the field geometry information represents, at least in part, a trajectory of a radiation source during administration of the radiation treatment plan.

4. The method of claim 1 wherein the control circuit is configured to determine weights for fields in the field geometry information to control an amount of radiation dose delivered at each field and to use the weights when optimizing the radiation treatment plan.

5. The method of claim 1 wherein the at least one isocenter that corresponds to the body outline comprises a plurality of isocenters that correspond to the body outline.

6. The method of claim 1 wherein the field geometry information corresponds to at least one of static-gantry fields, arc fields, fields with stereotactic radiosurgery cones, static-multi-leaf collimator fields, or dynamic-multi-leaf collimator fields.

7. The method of claim 1 wherein the control circuit is configured to determine relative radiation dose levels as a function of relative magnitudes of intersection volumes of field paths within healthy tissue.

8. The method of claim 7 wherein the control circuit is further configured to determine the intersection volumes as a function, at least in part, of geometrical solutions for common volumes of intersecting cylinders.

9. The method of claim 1 wherein the optimization information further comprises at least one of:
a model of a body outline for the particular patient;
dosimetric data comprising depth-dose profile data;
dosimetric data comprising depth-penumbra data.

10. An apparatus comprising:
a control circuit configured to:
access optimization information comprising:
at least one isocenter that corresponds to a body outline for a particular patient;
field geometry information for a particular radiation treatment platform; and
dosimetric data consisting of only depth-penumbra data and no more than one other dosimetric data;
optimize a radiation treatment plan for the particular patient using the particular radiation treatment platform as a function, at least in part, of the optimization information to provide an optimized radiation treatment plan wherein radiation dose levels delivered to the particular patient from a particular field depend on relative volume magnitude of field path intersections to thereby reduce radiation dose delivery to healthy patient tissue in regions having relatively more overlapping fields; and
operate the particular radiation treatment platform as a function of the optimized radiation treatment plan to administer radiation to the particular patient.

11. The apparatus of claim 10 wherein the dosimetric data only includes:
depth-dose profile data; and
the depth-penumbra data.

12. The apparatus of claim 10 wherein the field geometry information represents, at least in part, a trajectory of a radiation source during administration of the radiation treatment plan.

13. The apparatus of claim 10 wherein the control circuit is further configured to determine weights for fields in the field geometry information to control an amount of radiation dose delivered at each field and to use the weights when optimizing the radiation treatment plan.

14. The apparatus of claim 10 wherein the at least one isocenter that corresponds to the body outline comprises a plurality of isocenters that correspond to the body outline.

15. The apparatus of claim 10 wherein the field geometry information corresponds to at least one of static-gantry fields, arc fields, fields with stereotactic radiosurgery cones, static-multi-leaf collimator fields, or dynamic-multi-leaf collimator fields.

16. The apparatus of claim 10 wherein the control circuit is further configured to determine relative radiation dose levels as a function of relative magnitudes of intersection volumes of field paths within healthy tissue.

17. The apparatus of claim 16 wherein the control circuit is further configured to determine the intersection volumes as a function, at least in part, of geometrical solutions for common volumes of intersecting cylinders.

18. The method of claim 10 wherein the optimization information further comprises at least one of:
a model of a body outline for the particular patient;
dosimetric data comprising depth-dose profile data;
dosimetric data comprising depth-penumbra data.

* * * * *